United States Patent [19]
Allas et al.

[11] Patent Number: 5,879,682
[45] Date of Patent: *Mar. 9, 1999

[54] AFRAMONUM SEEDS FOR IMPROVING PENILE ACTIVITY

[76] Inventors: Soraya Allas, 4220 rue de Brébeuf, Montréal, Québec, Canada, H2J 3K7; Victor Ngoka, 5069 rue Berri, Montréal, Québec, Canada, H2J 2S1; Neil G. Hartman, 426 Elm avenue, Westmount, Québec, Canada, H3Y 3J1; Simon Owassa, 5875 Péloquin, Laval, Québec, Canada, H7H 2X1; Michel Ibea, 1575 rue Plessis, Montréal, Québec, Canada, H2L 2X6

[ * ] Notice: This patent issued on a continued prosecution application filed under 37 CFR 1.53(d), and is subject to the twenty year patent term provisions of 35 U.S.C. 154(a)(2).

[21] Appl. No.: 562,558

[22] Filed: Nov. 24, 1995

[51] Int. Cl.$^6$ .......................... A01N 65/00; A61K 35/78; A61K 39/385

[52] U.S. Cl. ........................................ 424/195.1; 514/960

[58] Field of Search .............................. 424/195.1; 514/2, 514/960

[56] References Cited

PUBLICATIONS

Galal, Int. J. of Pharmacognosy 34(1) pp. 64–69, 1996.
Cousins, Acta Zool Pathol Antverp (Belgium) Dec. 1976 (66) pp. 91–100 (Abstract), 1976.
Adegoke et al, Plant Foods Hum Nutr(Netherlands) Feb. 1994, 45(2) pp. 174–82 (Abstract), 1994.
Ayafor et al, Journal of Natural Products 57(7) Jul. 1994 pp. 917–923, 1994.
*The International Code of Botanical Nomenclature*, Werner Greuter et al. editors, 1994.
Newman and Northup, 1981, *Urol.*, 17:399–408.
Kaiser, 1988, *Am. J. Med.*, 85:147–152.
Virag, 1982, *Lancet*, vol. ii :938.
Krane et al, 1989, *N. Engl. J. Med.*, 321:1648–1659.
Morales et al., 1987, *J. Urol.*, 137:1168–72.
Susset et al., 1989, *J. Urol.*, 141:1360–1363.
Jan. 1995, *In La Lettre Médicale*, vol. 18, No. 20:89.
Earle et al, 1990, *J. Urol.*, 143:57–59.

*Primary Examiner*—Paula K. Hutzell
*Assistant Examiner*—Heather A. Bakalyar
*Attorney, Agent, or Firm*—Swabey Ogilvy Renault; France Côté

[57] ABSTRACT

The present invention relates to a pharmaceutical composition for improving penile rigidity and/or preventing erectile dysfunction, including premature ejaculation, of a male mammal patient which comprises at least one of seeds from Aframomum species, its closely related species and remote ancestors thereof, mixture thereof and extracts thereof. The pharmaceutical composition may further comprise a pharmaceutically acceptable carrier for topical or oral administration.

16 Claims, No Drawings

AFRAMONUM SEEDS FOR IMPROVING PENILE ACTIVITY

BACKGROUND OF THE INVENTION (a) Field of the Invention

The invention relates to pharmaceutical compositions based on the use of "Aframomum" seeds to solve the problem of male erectile dysfunction as well as premature ejaculation in men.

(b) Description of Prior Art

Mechanisms of erection

The penis is composed of a mass of erectile tissue enclosed in three cylindrical fibrous compartments. Penile erection is a haemodynamic event under autonomic nervous control. During the change from the flaccid condition of the organ to its erect state, there is increased blood flow filling the vascular spaces which results in tumescence. It is generally accepted that vasodilatation of the penile arteries rapidly followed by relaxation of the cavernous smooth muscle are primarily responsible for the initiation of erection (Newman and Northup, 1981, *Urol.*, 17:399–408).

There has been considerable progress in the understanding of the nervous control of the penile vasculature. Many neuropeptides including noradrenaline (NA), acetylcholine (ACh), adenosine 5'-triphosphate (ATP), serotonin 5-hydroxytryptamine (5-HT), as well as vasoactive intestinal polypeptide (VIP), calcitonin gene-related peptide (CGRP), neuropeptide Y (NPY), and substance P (SP), have been localized in perivascular nerves and considered as neurotransmitter candidates.

Causes of erectile dysfunction

Erectile dysfunction or impotence is common, affecting an estimated one in ten men, with prevalence much higher in certain subgroups: diabetics, smokers (Kaiser, 1988, *Am. J. Med.*, 85:147–152). It appears to be an age-related disorder with an incidence of 1.9% at the age of 40 and 25% at the age of 65 (Krane et al, 1989, *N. Engl. J. Med.*, 321:1648–1659).

The most common causes of impotence are generally classified as being of vascular, endocrine, neurological and psychogenic nature, but most often the exact mechanisms involved are not known. There is frequently an overlap between aetiologies, such as in diabetic patients who have both vascular and neurological complications contributing to impotence. Furthermore, there is often a psychogenic component in patients with a distinct organic cause of impotence.

Drug therapy of erectile dysfunction

Endocrinal causes of impotence, constituting less than 10% of total causes of impotence, can be successfully treated by medical therapy. In all other causes, drug therapy has not been satisfactory and a few drugs and/or drug combinations have gained clinical acceptance. These drugs are vasodilators, they include yohimbine, papaverine, papaverine and phentolamine in combination and prostaglandin E1.

Yohimbine and phentolamine are known to be an alpha-adrenoreceptor blocker. Yohimbine is available for oral use. It has first appeared to have promising value but recently, several studies revealed a marginal and non significant effect (Morales et al., 1987, *J. Urol.*, 137:1168–72; Susset et al., 1989, *J. Urol.*, 141:1360–1363). Furthermore, yohimbine may induce hypertension, rashes and panic attacks. It is important to note that yohimbine is not licensed in the United Kingdom and has never been approved by the United States FDA (January 1995, *In La Lettre Médicale*, Vol. 18, No. 20:89).

Papaverine is often characterized as a non-specific vasodilator, and its cellular mechanism of action is unclear. It is an intracorporeally administered drug and its efficiency is better than yohimbine. However, it is well known that an intracavernosal injection of papaverine can produce major side effects such as prolonged painful erection. Other side effects include fibrosis and bruising at the site of injection and liver function abnormalities among others (Virag, 1982, *Lancet*, vol. ii:938). Moreover, many patients are disenchanted with the long-term injection involved in intracavernosal pharmacotherapy, finding the technique artificial, lacking in spontaneity and being time consuming.

Prostaglandin E1 (PGE1) is also administered intracavernosally. Some studies have shown PGE1 to be as effective as papaverine or the papaverine/phentolamine combination (Earle et al, 1990, *J. Urol.*, 143:57–59), but like papaverine and yohimbine it also causes undesirable effects including local pain and prolonged erection.

It would be highly desirable to be provided with a painless therapy for male erectile dysfunction as well as for premature ejaculation in male without the drawbacks of the prior art techniques.

SUMMARY OF THE INVENTION

One aim of the present invention is to provide a painless therapy for male erectile dysfunction as well as for premature ejaculation in male without the drawbacks of the prior art techniques.

The composition of the present invention provide a painless and safe medication to patients suffering from erectile dysfunction and premature ejaculation as well as to men wishing to improve their sexual performance.

"Aframomum" is a broad genus of plants found in the humid tropics of Africa, which includes more than 50 species known to date. The Aframomum species all belong to the family of Zingiberaceae. However, there have been much confusion due to poor material, mixed gatherings, and unfamiliarity with the genus in the field. To date the genus Aframomum is employed as a spice, in perfumes and dyes, and currently in the treatment of hemorrhoids in Africa where some of them are widely cultivated for their edible spicy fruit. In some species, leafs are well known to be dispensed for measles and externally for leprosy, while a root decoction is taken by nursing mothers to inhibit excessive lactation and to control postpartum hemorrhage.

Rhizomes of other species are used as ingredient for the preparation of remedy for infertility, to promote conception and the fresh fruits are used some times as tonic for sexual stimulation. Several plants in the genus are also used as purgative, galactogogue and anthelmintic and as hemostatic agent. Seeds of some species are also used with leaves of *Urera oblongifolia* as an external treatment for tumors. In Senegal, seeds of *Aframomum melegueta* are usually mixed with salt and rubbed to the interior of the mouth as treatment of sleeping sickness.

Antimicrobial activity have also been reported for seed constituents of *Aframomum danielli*, but, no species of the genus, has ever been reported on its seed abilities to reestablish erectile function and/or to improve penile rigidity in men.

The invention provides a new application of Aframomum plants in improving male penile rigidity, and/or treating male erectile dysfunction and premature ejaculation.

In accordance with the present invention there is provided a pharmaceutical composition for improving penile rigidity and/or treating erectile dysfunction, as well as premature ejaculation, of a male mammal patient which comprises:

at least one type of seeds selected from the group consisting of *Aframomum stipulatum, Aframomum geocarpum, Aframomum usambarence*, its closely or related species, and remote ancestors thereof, mixture thereof and extracts thereof.

The pharmaceutical composition of the present invention may include a pharmaceutically acceptable carrier for topical or oral administration.

The pharmaceutical composition of the present invention is not aphrodisiac but may be used both by healthy and non-healthy men to improve penile rigidity, or to delay ejaculation. The pharmaceutical composition of the present invention can also be used to prevent premature ejaculation.

The abbreviations used herein are defined as follows.

AF Aframomum

AFS *Aframomum stipulatum*

The nomenclature used to define plants is that specified by Werner Greuter (the International code of botanical nomenclature, 1994), wherein, in accordance with conventional methods, the genus appears on the left, while the specie is written on the right.

The term "male mammal patient" as used herein is intended to mean a mammal selected from the group consisting of human, equine, caprine, bovine, canine and feline.

The term "healthy men" as used herein is intended to mean a men which show no penile erectile dysfunction.

The term "non-healthy" men as used herein is intended to mean a men bearing erectile dysfunction.

DETAILED DESCRIPTION OF THE INVENTION

The present invention relates to an oral or topical composition for the treatment of male erectile dysfunction which comprises Aframomum. The present invention relates particularly to the Aframomum seeds ability to delay male ejaculation and to ensure full erection The pharmaceutical composition of present invention are intended for oral or topical administration which constitutes one of the main advantages of the present invention with respect to the prior art therapy.

In addition, for men seeking post-ejaculation penile performance, the composition of the present invention may optionally be used with alcoholic beverages to synergistically maintain libido, whereas successive ejaculation/reerection can easily be done for several times with constant penile rigidity.

In accordance with the present invention any of the following Aframomum seeds may be used alone or in combination:

*Aframomum stipulatum, Aframomum angustifolium, Aframomum alpinum, Aframomum atewae, Aframomum amanience, Aframomum alboviolacium, Aframomum baumannii, Aframomum biauriculatum, Aframomum cordifolium, Aframomum citratum, Aframomum chlamydanthum, Aframomum crassilabium, Aframomum clusii, Aframomum elliotti, Aframomum elegans, Aframomum exscatum, Aframomum erythrostachyum, Aframomum tectorum, Aframomum hanburyi, Aframomum korarima, Aframomum kayserianum, Aframomum kenience, Aframomum limbatum, Aframomum luteoalbum, Aframomum latifolium, Aframomum letestuanum, Aframomum longiscapum, Aframomum leptolepis, Aframomum longiscapum, Aframomum macrospermum, Aframomum mala, Aframomum mildbreadii, Aframomum meleguetella, Aframomum melegueta, Aframomum pruisonum, Aframomum polyathum, Aframomum pilosum, Aframomum erythrocarpum, Aframomum flavum, Aframomum glaucophyllum, Aframomum gigantum, Aframomum geocarpum, Aframomum granumparadisi, Aframomum rostratum, Aframomum stanfieldii, Aframomum strobilaceum, Aframomun sanguineum, Aframomum sulcatum, Aframomum sceptrum, Aframomum subsericeum, Aframomum usambarence, Aframomum zambesiacum, Aframomum zimmerannii, Aframomum daniellii* and their closely related or remote ancestors.

In accordance with a preferred embodiment of the present invention at least two of the foregoing Aframomums or the seed extracts of the foregoing Aframomums may be used as active ingredients in the composition for improvement of penile rigidity and/or treatment of male erectile dysfunction and premature ejaculation.

In accordance with the present invention a wide range of Aframomum seeds may be used, which are the seeds of unnamed Aframomum consisting of the remote ancestors of the foregoing Aframomums as an active ingredient in the composition for improvement of penile rigidity and/or treatment of male erectile dysfunction and premature ejaculation.

In accordance with the present invention a wide range of Aframomum seeds may be used, which are the seeds of unknown Aframomums and unknown related species as an active ingredient in the composition for improvement of penile rigidity and/or treatment of male erectile dysfunction and premature ejaculation.

The use of Aframomum seeds of the present invention and the composition of the present invention are beneficial in that:

- it is intended for oral or topical administration in both healthy and non-healthy men;
- it will not cause any undesirable erection, or affect any sexual behavior or need, even for men without a sexual partner;
- it will not cause priapism, or any other sexual side effect during or after its use;
- for any degree or kind of impotence, it reestablishes the male erectile function and maintains constant penile rigidity during the sexual act;
- it significantly increases and constantly maintains the penile rigidity in healthy men, during their sexual relationships; and
- the composition of the present invention may be used by both healthy and non-healthy men to delay penile ejaculation, and/or to increase penile rigidity.

The pharmaceutical composition of the present invention is characterized in that:

- it is not aphrodisiac, unlike as mentioned when describing the fresh fruit of *Aframomum melegueta*, but it allow constant penile rigidity while delaying ejaculation in both healthy and non-healthy men;
- it is highly potent in terms of penile rigidity and may act synergistically with alcoholic beverages to maintain sufficient libido and to ensure successive ejaculation/reerection processes;
- it prevents premature ejaculation while improving constant penile rigidity; and
- it allows men to maintain both libido and penile rigidity at such a level that no erection failure does occur during the sexual relationship.

The composition of the present invention can also be used in mixtures with hormones such as testosterone and/or other agents to synergistically improve the reestablishment of male penile function.

PREFERRED EMBODIMENTS

One of the preferred embodiment of the present invention relates to composition comprising the seeds of Aframomum species which contain benzenoids of molecular weight between 100 and 500, preferably paradol, gingerol and/or shagaol in their chemical composiion.

Another preferred embodiment of the present invention relates to composition comprising the seeds of Aframomum species which contain terpenoids of molecular weight between 100 and 600, preferably labdane diterpenoid in their chemical composition.

Still another preferred embodiment of the present invention relates to composition comprising the seeds of Aframomum species which contain flavonoids or quinoids of molecular weight between 100 and 600 and/or the foregoing benzenoids or terpenoids in their chemical composition.

One of the preferred embodiments of the present invention relates to composition comprising the seeds of *Aframomum geocarpum* and its closely related species or ancestors.

The most preferred embodiment of the present invention relates to composition comprising the seeds of *Aframomum strobilaceum* or *Aframomum usambarence* and their closely related species or ancestors.

Another preferred embodiment of the present invention relates to composition comprising the seeds of the remote ancestors of *Aframomum melegueta* and their closely related species containing paradol, shagaol or gingerol.

The most preferred embodiment of the present invention relates to composition comprising the seeds of *Aframomum stipulatum* and its closely related species or ancestors.

includes any pharmaceutically acceptable adjuvant, such as known thickening agents (natural or synthetic) or diluting agents to form a dosage form of the pharmaceutical composition which consists of a suspension of the active ingredient. Preferably, such thickening agents are tragacanth mucilage and colloidal silicon dioxide. Diluting agents which may be used are powders and ointment for the topical application of the pharmaceutical composition. Moreover, other oral dosage form may be used, which include without limitation, capsules lozenges, pastilles, molded or pressed tablets, among others.

The present invention will be more readily understood by referring to the following example which is given to illustrate the invention rather than to limit its scope.

EXAMPLE I

Encapsulation

Seeds of *Aframomum stipulatum* (imported from Brazzaville, Congo) are scrupulously washed with water and sterilized for 30 min. under U.V. at 254 nm. After drying, 1 mg/kg of *Aframomum stipulatum* seeds, properly milled are carefully encapsulated in a sterile hoad class II, Type A/B$_3$ (The Baker Company, Sanford, Me.).

Posology

Healthy men:
  3 times a day: 1 capsule is taken each 4 to 6 hours.

Non-healthy men:
  3 times a day: 2 to 3 capsules are taken each 4 to 6 hours.

Evidence of the improved penile rigidity in healthy men as well as evidence of delayed ejaculation are clearly shown in Table 1.

TABLE 1

*Aframomum stipulatum* composition improving penile activity in healthy men

| Volunteer code: | Age (years) | Weight (Kg) | Race | Before AFS seeds intake | During AFS seeds intake | After AFS seeds intake | AFS Seeds penile effects | |
|---|---|---|---|---|---|---|---|---|
| | | | | | | | Penile rigidity | Ejaculation delay |
| V-H01-O | 37 | 96 | B | 130/84 | 135/82 | 132/85 | ++[b] | = |
| V-S02-N | 30 | 65 | W | 112/69 | 114/65 | 115/67 | ++[a] | ++ |
| V-O01-K | 28 | 75 | B | NA | NA | NA | ++[b] | ++ |
| V-G04-V | 34 | 82 | W | 118/70 | 121/72 | 124/74 | ++[a] | + |
| V-J05-B | 28 | 76 | B | 116/68 | 118/66 | 120/68 | + | = |
| V-O06-H | 23 | 65 | B | 124/69 | 125/70 | 127/72 | ++[a] | + |
| V-P07-B | 35 | 79 | W | NA | NA | NA | ++[b] | ++ |
| V-E08-D | 23 | 69 | W | 119/72 | 120/73 | 123/73 | ++[a] | ++ |
| V-N09-D | 26 | 76 | B | 125/76 | 122/75 | 125/72 | + | = |
| V-B10-K | 28 | 85 | B | 123/72 | 123/74 | 124/76 | ++[a] | ++ |
| V-M11-A | 31 | 86 | W | NA | NA | NA | ++[a] | + |
| V-J12-C | 35 | 76 | B | NA | NA | NA | ++[a] | ++ |
| V-A13-D | 32 | 85 | B | NA | NA | NA | ++[a] | + |
| V-814-C | 40 | 77 | W | 120/71 | 122/70 | 119/72 | ++[a] | + |
| V-A15-B | 35 | 85 | B | NA | NA | NA | ++[b] | ++ |

The preferred dosage of the composition of the present invention contains between about 0.3 mg/kg to about 10 mg/kg of the seeds of Aframomum species per weight of the patient, most preferably between about 1 mg/kg to about 6 mg/kg. The composition intake may be daily, twice daily or up to three times daily depending on the patient's condition.

The preferred pharmaceutically acceptable carrier which may be used in accordance with the present invention All data are provided under testimony of both the male and the female.

= The *Aframomum stipulatum* effect is equal to that usually observed by the male during normal conditions.

+ The *Aframomum stipulatum* effect is higher than that usually observed by the male in normal conditions.

++ The *Aframomum stipulatum* effect is much higher than that usually observed by the male during normal conditions.
NA: non-available data
W: White
B: Black
Systolic/Diastolic: the brachial systolic pressure average versus the diastolic pressure average in mmHg. Pressure were measured each 30 min. for (2 hours before AFS intake), (6 hours during AFS intake), and (2 hours more after AFS intake) on a digital blood pressure meter.
++[a]: data provided under testimony of both sexual partners: AFS intake allow these men to exhibit very high and constant penile rigidity.
++[b]: data provided under testimony of both sexual partners: AFS intake with alcoholic beverage (2×375 ml Molson Dry™, a light beer from Molson Canada), allow these men to exhibit more than 3 successive ejaculation/reerection steps with constant libido and penile rigidity.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A pharmaceutical composition comprising milled seeds from *Aframomum stipulatum* or extracts therefrom in association with a pharmaceutical carrier, wherein said composition is in a molded or pressed tablet or capsule form.

2. A method for improving penile rigidity of a human male, said method comprising the step of administering the pharmaceutical composition of claim 1 to said male in an amount effective to increase penile rigidity.

3. The method of claim 2, wherein the composition is administered at a dosage of about 0.3 mg to about 10 mg per kg of the male's body weight.

4. The method of claim 3, wherein the pharmaceutical composition is administered at a dosage of about 1 mg to about 6 mg per kg of the male's body weight.

5. The method of claim 3 wherein the pharmaceutical composition is administered once, twice or three times daily.

6. A method for improving penile function of a human male, said method comprising the step of administering the pharmaceutical composition of claim 1 to said male in an amount effective to delay ejaculation.

7. The method of claim 6 wherein the pharmaceutical composition is administered at a dosage of about 0.3 mg to about 10 mg per kg of the male's body weight.

8. The method of claim 7, wherein the pharmaceutical composition is administered at a dosage of about 1 mg to about 6 mg per kg of the male's body weight.

9. The method of claim 7 wherein the pharmaceutical composition is administered once, twice or three times daily.

10. A method for improving post-ejaculation penile function of a human male during sexual relations, said method comprising the steps of administering the pharmaceutical composition of claim 1 in combination with alcoholic beverage to said male in an amount effective to achieve multiple successive ejaculation/reerection processes with constant penile rigidity.

11. The method of claim 10, wherein the pharmaceutical composition is administered at a dosage of about 0.3 mg to about 10 mg per kg of the male's body weight.

12. The method of claim 11, wherein the pharmaceutical composition is administered at a dosage of about 1 mg to about 6 mg per kg of the male's body weight.

13. A method for treating erectile disfunction of a human male, said method comprising the step of administering the pharmaceutical composition of claim 1 to said male in an amount effective to increase penile rigidity or delay ejaculation.

14. The method of claim 13, wherein the pharmaceutical composition is administered at a dosage of about 0.3 mg to about 10 mg per kg of the male's body weight.

15. The method of claim 14, wherein the pharmaceutical composition is administered at a dosage of about 1 mg to about 6 mg per kg of the male's body weight.

16. The method of claim 14 wherein the pharmaceutical composition is administered once, twice or three times daily.

* * * * *

UNITED STATES PATENT AND TRADEMARK OFFICE
CERTIFICATE OF CORRECTION

PATENT NO. : 5,879,682
DATED : March 9, 1999
INVENTOR(S) : Soraya Allas, et al.

It is certified that error appears in the above-identified patent and that said Letters Patent is hereby corrected as shown below:

Title page, item [54], and col.1, line 1

"AFRAMONUM" should read --AFRAMOMUM--.
item [73] is missing; please add the name of the Assignee "PEYA BIOTECH INC."

Signed and Sealed this

Twenty-sixth Day of October, 1999

Attest:

Q. TODD DICKINSON

Attesting Officer

Acting Commissioner of Patents and Trademarks